(12) United States Patent
Herron et al.

(10) Patent No.: US 7,365,230 B2
(45) Date of Patent: Apr. 29, 2008

(54) CROSS-LINKABLE POLYMERS AND ELECTRONIC DEVICES MADE WITH SUCH POLYMERS

(75) Inventors: Norman Herron, Newark, DE (US); Gary A. Johansson, Hockessin, DE (US); Nora Sabina Radu, Landenberg, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 59 days.

(21) Appl. No.: 10/783,304

(22) Filed: Feb. 20, 2004

(65) Prior Publication Data

US 2005/0184287 A1   Aug. 25, 2005

(51) Int. Cl.
   C07C 211/54   (2006.01)
(52) U.S. Cl. .................................... 564/309; 430/73
(58) Field of Classification Search .............. None
   See application file for complete search history.

(56) References Cited

U.S. PATENT DOCUMENTS

| | | | |
|---|---|---|---|
| 4,086,209 A | | 4/1978 | Hara et al. |
| 4,665,000 A | * | 5/1987 | Tokoli et al. ............... 430/85 |
| 5,652,067 A | | 7/1997 | Ito et al. |
| 5,677,097 A | | 10/1997 | Nukada et al. |
| 5,929,194 A | | 7/1999 | Woo et al. |
| 5,994,573 A | | 11/1999 | Tachikawa et al. |
| 6,020,426 A | | 2/2000 | Yamaguchi et al. |
| 6,107,439 A | | 8/2000 | Yanus et al. |
| 6,107,452 A | | 8/2000 | Miller et al. |
| 6,132,913 A | | 10/2000 | Fuller et al. |
| 6,143,452 A | | 11/2000 | Sakimura et al. |
| 6,376,695 B1 | | 4/2002 | Kushibiki et al. |
| 6,558,818 B1 | | 5/2003 | Samuel et al. |
| 2001/0017155 A1 | | 8/2001 | Bellmann et al. |
| 2002/0050597 A1 | | 5/2002 | Hirose et al. |
| 2002/0055014 A1 | | 5/2002 | Okada et al. |
| 2002/0057050 A1 | | 5/2002 | Xiaobo |
| 2003/0099862 A1 | | 5/2003 | O'Neill et al. |
| 2003/0162053 A1 | | 8/2003 | Marks et al. |
| 2003/0224205 A1 | | 12/2003 | Li et al. |
| 2003/0225234 A1 | | 12/2003 | Jaycox et al. |
| 2003/0232264 A1 | | 12/2003 | Tokarski et al. |
| 2004/0004433 A1 | | 1/2004 | Lamansky et al. |

FOREIGN PATENT DOCUMENTS

| | | |
|---|---|---|
| EP | 1 154 331 A1 | 11/2001 |
| EP | 1 284 258 A2 | 2/2003 |
| EP | 1 464 691 A | 10/2004 |
| JP | 2004030942 A2 * | 1/2004 |
| WO | WO 02/01653 A | 1/2002 |
| WO | WO 2004/005406 A | 1/2004 |

OTHER PUBLICATIONS

Schmitz et al. Advanced Materials 1999, 11, No. 10 p. 821-826.*
Indictates that the CAS Abstract is attached.*
Bacher, Andreas et al., Photo-Corss-Linked Triphenylenes as Novel Insoluble Hole Transport Materials in Organic LEDs, Macromolecules, 1999, 4551-4557, 32, American Chemical Society.
Nuyken, Oskar et al., Crosslinkable hole- and electron-transport materials for application in organic light emitting devices (OLEDs), Designed Monomers and Polymers, 2002, 195-210, 5(2,3).
M. Thelakkat et al., Synthesis and Properties of Novel Hole Transport Materials for Electroluminescent Devices, Macromolecular Symposia, Wiley VCH, Weinheim, DE, vol. 125:157-164, 1998, XP000738958.
International Search Report & Written Opinion of the International Searching Authority Dated: Jun. 30, 2005, International Appln. No. PCT/US2005/005584, International Filing Date: Feb. 17, 2005, 12 Pages.

* cited by examiner

Primary Examiner—Kamal A. Saeed
Assistant Examiner—Jason M Nolan
(74) Attorney, Agent, or Firm—John H. Lamming

(57) ABSTRACT

The present invention relates to novel cross-linkable polymers and a wide variety of electronic devices containing at least one layer having the polymer. The compounds can function as monomers, and copolymers can be formed from such monomers, such copolymers comprising, as polymerized units, a plurality of units of the compounds.

26 Claims, 1 Drawing Sheet

CROSS-LINKABLE POLYMERS AND ELECTRONIC DEVICES MADE WITH SUCH POLYMERS

BACKGROUND OF THE INVENTION

1. Field of the Invention

The present invention relates to novel compounds useful as hole transport materials in making electronic devices. The invention further relates to electronic devices having at least one active layer comprising such a hole transport material.

2. Background

In organic photoactive electronic devices, such as organic light emitting diodes ("OLED"), that make up OLED displays, the organic active layer is sandwiched between two electrical contact layers in an OLED display. In an OLED the organic photoactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used.

Devices that use photoactive materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode.

Production of electronic devices, including photo-active devices, relies on certain properties in materials used in the devices, including film-forming ability, solubility, and thermal stability. Moreover, it is often desirable that materials have reduced solubility when they are used in forming multiple layers in a device.

There is a continuing need for charge transport materials for use in electronic devices.

SUMMARY OF THE INVENTION

The compounds disclosed herein are useful in making charge transport layers for use in electronic devices. The charge transport layers can be used in any application wherein charge transport capacity is desired. Examples of some uses include, but are not limited to, organic light-emitting diodes ("OLED"s), photovoltaic cells, light sensors, thin film organic transistors, photoconductors, and electrophotographic applications.

Examples of other organic electronic devices that may benefit form having one or more layers comprising the new compounds and compositions described herein include: (1) devices that convert electrical energy into radiation (e.g., a light-emitting diode, light emitting diode display, or diode laser), (2) devices that detect signals through electronics processes (e.g., photodetectors (e.g., photoconductive cells, phototoresistors, phototswitches, phototransistors, phototubes), IR detectors), (3) devices that convert radiation inot electrical energy, (e.g., a photovoltaic device or solar cell), and (4) devices that include one or more electronic components that include one or more organic semi-conductor layers (e.g., a transistor or diode).

The compositions and methods disclosed herein allow the reduction of solubility of a compound for use in an electronic device after deposition of the material to form a layer in the device. The compounds disclosed herein are crosslinkable, i.e., crosslinking can be induced in the compounds due to the incorporation within the compounds of crosslinkable groups.

Examples of crosslinkable groups include substituted vinyl groups, acrylate groups (e.g. ethenyl ($CH_2$=CH—)), propenyl (($CH_3$)(H)C=CH—), acryloyl ($CH_2$=CH—C(O)—O—), and methacryloyl ($CH_2$=C($CH_3$)—C(O)—O—), cyclic ethers and siloxanes. In addition, a crosslinkable or "crosslinking" group can be any organic fragment that can bind to a preformed support, and that can be further polymerized after it is bound to the support. Generally, any polymerizable group can function as a crosslinkable group. Any organic or inorganic material can be used as a support as long as it meets desired solubility properties, and has reactive sites that can covalently link a compound to the surface thereof. Such materials are well known and include polystyrene, polyalcohols, polyacrylates, polysilanes and polysiloxanes.

One aspect of the present invention is a compound having the formula (I):

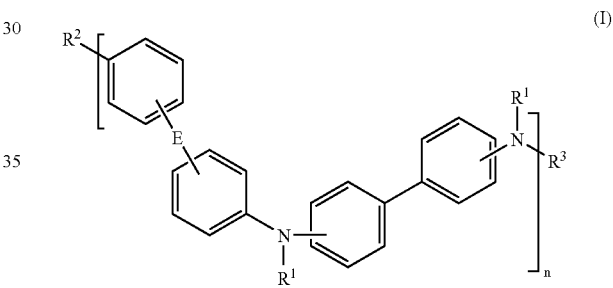

wherein n is an integer of at least 1 and $R^1$ is selected from aryl, heteroaryl, fluoroaryl, and fluoroheteroaryl substituted with 1 or more fluorine atoms, for example, up to 7 fluorine atoms, and a crosslinkable group attached to aryl, heteroaryl, fluoroaryl, and fluoroheteroaryl substituted with 1 or more fluorine atoms, for example, up to 7 fluorine atoms. The compound comprises more than one group $R^1$, and $R^1$ can be different at each occurrence. For example, the compound represented by formula (I) can function as a monomer, and copolymers can be formed from the compound, such copolymers comprising, as polymerized units, a plurality of units having formula (I) in which at least one unit contains $R^1$ different from $R^1$ in other units. In some embodiments, $R^1$ is aryl.

$R^3$ is selected from H and $R^1$. $R^2$ is selected from H, aryl, alkyl, fluoroalkyl, Cl, Br, I, heteroaryl, fluoroaryl, and fluoroheteroaryl substituted with 1 or more fluorine atoms, for example, up to 7 fluorine atoms, a crosslinkable group attached to aryl, heteroaryl, fluoroaryl, fluoroheteroaryl substituted with 1 or more fluorine atoms, for example, up to 7 fluorine atoms a crosslinkable group, and an arylamino group of formula (II),

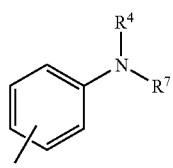
(II)

wherein R⁴ is selected from aryl, H, R¹, alkyl, and fluoroalkyl. In some embodiments R⁴ is aryl. R⁷ is selected from aryl, heteroaryl, fluoroaryl, fluoroheteroaryl substituted with 1 or more fluorine atoms, for example, up to 7 fluorine atoms, and a crosslinkable group attached to aryl, heteroaryl, fluoroaryl, and fluoroheteroaryl substituted with 1 or more fluorine atoms, for example up to 7 fluorine atoms.

In some embodiments, $R^2$ is H. In some embodiments, $R^2$ is different from $R^3$. In some embodiments, $R^2$ is H and $R^3$ is aryl. In some embodiments, when $R^1$ or $R^3$ are directly bound to a nitrogen atom, the crosslinkable group is not a vinyl group.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, fluoroaryloxy, a crosslinkable group, and a crosslinkable group attached to alkyl, aryl, alkoxy, aryloxy, fluoroalkyl, fouoroaryl, fluoroalkoxy, or fluoroaryloxy, and wherein $R^5$ and $R^6$ can, when taken together, form a non-aromatic ring, and E is $(CR^5R^6)_m$, such that when n is greater than 1 and m is 1, at least one of $R^5$ and $R^6$ is not hydrogen or a hydrocarbon.

In some embodiments, at least one aromatic ring in the compound of formula (I) has one or more substituents independently selected from H, F, alkyl, aryl, alkoxy, aryloxy, fluoroalkyl, fluoroaryl, fluoroalkoxy, fluoroaryloxy, and crosslinkable groups. In further embodiments, substituents on two neighboring aromatic rings in the compound of formula (I) can together form an aromatic or non-aromatic ring. Neighboring aromatic rings can be adjacent or vicinal. In further embodiments, adjacent substituents on a single ring can be linked to form a fused aromatic or non-aromatic ring.

In some embodiments, $R^1$ is selected from phenyl, 1-naphthyl, and 2-naphthyl. In some embodiments, $R^1$ is selected from cinnamate and chalcone groups. In some embodiments, n=1, $R^2$ is H, and $R^3$ is selected from phenyl, 1-naphthyl and 2-naphthyl.

Another aspect of the invention is a composition comprising a compound having formula (I) as defined hereinabove.

Another aspect of the present invention is a compound of formula
(III)

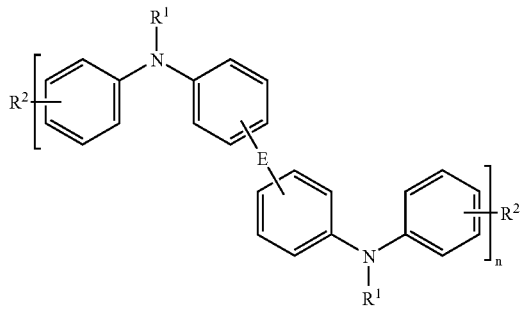

wherein n is an integer of at least 1, $R^1$ is selected from aryl, heteroaryl, fluoroaryl, and fluoroheteroaryl substituted with 1 or more fluorine atoms, for example, up to 7 fluorine atoms, and a crosslinkable group attached to aryl, heteroaryl, fluoroaryl, and fluoroheteroaryl substituted with 1 or more fluorine atoms, for example, up to 7 fluorine atoms. $R^1$ may be different at each occurrence (i.e. copolymers). $R^2$ is selected from H, aryl, alkyl, fluoroalkyl, Cl, Br, I, heteroaryl, fluoroaryl, and fluoroheteroaryl substituted with 1 or more fluorine atoms, for example, up to 7 fluorine atoms, a crosslinkable group attached to aryl, heteroaryl, fluoroaryl, fluoroheteroaryl substituted with 1 or more fluorine atoms, for example, up to 7 fluorine atoms, a crosslinkable group, and arylamino of formula (II). In some embodiments, when $R^1$ or $R^3$ are directly bound to a nitrogen atom, the crosslinkable group is not a vinyl group. In some embodiments, $R^2$ is H or aryl. $R^4$ is selected from aryl, H, $R^1$, alkyl, fluoroalkyl. In some embodiments $R^4$ is aryl. $R^7$ is selected from aryl, heteroaryl, fluoroaryl, fluoroheteroaryl substituted with 1 or more fluorine atoms, for example up to 7 fluorine atoms and a crosslinkable group attached to aryl, heteroaryl, fluoroaryl, and fluoroheteroaryl substituted with 1 or more fluorine atoms, for example up to 7 fluorine atoms.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, fluoroaryloxy, a crosslinkable group, and a crosslinkable group attached to alkyl, aryl, alkoxy, aryloxy, fluoroalkyl, fouoroaryl, fluoroalkoxy, or fluoroaryloxy, and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments, at least one aromatic ring in the compound of formula (III) has a substituent selected from H, F, alkyl, aryl, alkoxy, aryloxy, fluoroalkyl, fluoroaryl, fluoroalkoxy, fluoroaryloxy, and a crosslinkable group. In further embodiments, substituents on two neighboring aromatic rings in the compound of formula (III) can together form an aromatic or non-aromatic ring. In further embodiments, adjacent substituents on a single ring can be linked to form a fused aromatic or non-aromatic ring.

In some embodiments, $R^1$ is selected from phenyl, 1-naphthyl, and 2-naphthyl. In some embodiments, n=1, and $R^2$ is arylamino of formula (II), wherein $R^4$ is selected from aryl, H, $R^1$, alkyl, and fluoroalkyl. In some embodiments, n=1, $R^1$ is selected from phenyl, 1-naphthyl or 2-naphthyl and $R^2$ is a cinnamyl group. In some embodiments, n=1, $R^1$ is selected from phenyl, 1-naphthyl or 2-naphthyl and $R^2$ is arylamino of formula (II), wherein $R^4$ is selected from aryl, H, or cinnamate. In some embodiments, $R^1$ is selected from phenyl, 1-naphthyl or 2-naphthyl and $R^2$ is selected from H or aryl and E is selected from $(CR^5R^6)_m$, wherein $R^5$ is selected from alkyl, aryl, alkoxy and $R^6$ is a crosslinkable group.

Another aspect of the present invention is a composition comprising a compound of formula (III) as defined hereinabove.

Another aspect of the present invention is a compound of formula

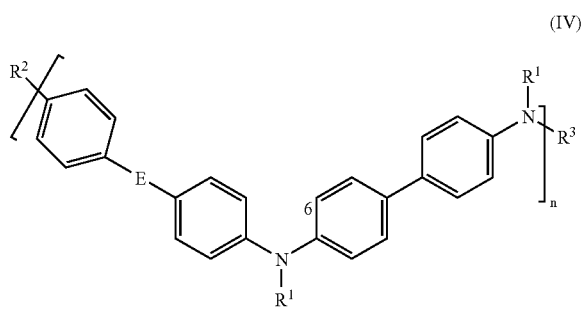

(IV)

wherein:

R[1] is selected from aryl, heteroaryl, fluoroaryl, and fluoroheteroaryl substituted with 1 or more fluorine atoms, for example, up to 7 fluorine atoms, and a crosslinkable group attached to aryl, heteroaryl, fluoroaryl, and fluoroheteroaryl substituted with 1 or more fluorine atoms, for example, up to 7 fluorine atoms, and may be different at each occurrence (i.e. copolymers). In some embodiments, R[1] is aryl. R[2] is selected from H, aryl, alkyl, fluoroalkyl, Cl, Br, I, heteroaryl, fluoroaryl, and fluoroheteroaryl substituted with 1 or more fluorine atoms, for example, up to 7 fluorine atoms, a crosslinkable group attached to aryl, heteroaryl, fluoroaryl, fluoroheteroaryl substituted with 1 or more fluorine atoms, for example, up to 7 fluorine atoms, a crosslinkable group, and arylamino of formula (II). In some embodiments, when R[1] or R[3] are directly bound to a nitrogen atom, the crosslinkable group is not a vinyl group. In some embodiments, R[2] is H or aryl. R[4] is selected from aryl, H, R[1], alkyl, fluoroalkyl. In some embodiments R[4] is aryl. R[7] is selected from aryl, heteroaryl, fluoroaryl, fluoroheteroaryl substituted with 1 or more fluorine atoms, for example up to 7 fluorine atoms and a crosslinkable group attached to aryl, heteroaryl, fluoroaryl, and fluoroheteroaryl substituted with 1 or more fluorine atoms, for example up to 7 fluorine atoms.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein R[5] and R[6] are each independently selected from H, F, alkyl, aryl, alkoxy, aryloxy, fluoroalkyl, fluoroaryl, fluoroalkoxy, fluoroaryloxy, a crosslinkable group, and a crosslinkable group attached to alkyl, aryl, alkoxy, aryloxy, fluoroalkyl, fouoroaryl, fluoroalkoxy, or fluoroaryloxy, and wherein R[5] and R[6] can, when taken together, form a non-aromatic ring, provided that when E is $(CR^5R^6)_m$, and n is greater than 1 and m is 1, at least one of R[5] and R[6] is not hydrogen or a hydrocarbon.

In some embodiments, at least one aromatic ring in the compound of formula (I) has a substituent selected from H, F, alkyl, aryl, alkoxy, aryloxy, fluoroalkyl, fluoroaryl, fluoroalkoxy, fluoroaryloxy and a crosslinkable group. In some embodiments, R[1] is selected from phenyl, 1-naphthyl, and 2-naphthyl. In some embodiments, n=1, R[2] is H, and R[3] is selected from phenyl, 1-naphthyl and 2-naphthyl. In some embodiments, n=1, R[1] is selected from phenyl, 1-naphthyl and 2-naphthyl and R[2] is a cinnamyl group.

Another aspect of the invention is a composition comprising a compound having formula (IV) as defined hereinabove.

Another aspect of the present invention is a composition comprising copolymers prepared by copolymerizing at least one functional monomer having the formula (I) or (III) as defined hereinabove with at least one crosslinkable group as defined above. The polymerization can be performed using thermal or photochemical polymerization methods.

The crosslinking can take place during or after polymerization. In one embodiment, R[2] is a photosensitive or thermally sensitive group and crosslinking can be initiated after polymerization of one or more monomers of formula (I). Polymers having these groups can be formed into films, and then treated with heat or actinic radiation to crosslink. Crosslinked films are generally more robust and resistant to solvents that may be used in later processing steps. Crosslinking groups are well known, and any can be used so long as they do not detrimentally affect the desired properties of the polymer.

Another embodiment is an electronic device having at least one layer comprising a composition having the formula:

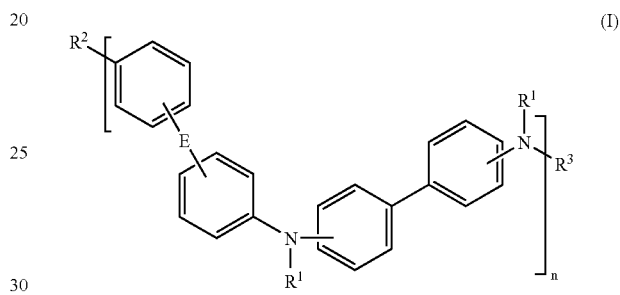

(I)

wherein n is an integer of at least 1 and R[1] is selected from aryl, heteroaryl, fluoroaryl, and fluoroheteroaryl substituted with 1 or more fluorine atoms, for example, up to 7 fluorine atoms, and a crosslinkable group attached to aryl, heteroaryl, fluoroaryl, and fluoroheteroaryl substituted with 1 or more fluorine atoms, for example, up to 7 fluorine atoms. The compound comprises more than one group R[1], and R[1] can be different at each occurrence. For example, the compound represented by formula (I) can function as a monomer, and copolymers can be formed from the compound, such copolymers comprising, as polymerized units, a plurality of units having formula (I) in which at least one unit contains R[1] different from R[1] in other units. In some embodiments, R[1] is aryl.

R[3] is selected from H and R[1]. R[2] is selected from H, aryl, alkyl, fluoroalkyl, Cl, Br, I, heteroaryl, fluoroaryl, and fluoroheteroaryl substituted with 1 or more fluorine atoms, for example, up to 7 fluorine atoms, a crosslinkable group attached to aryl, heteroaryl, fluoroaryl, fluoroheteroaryl substituted with 1 or more fluorine atoms, for example, up to 7 fluorine atoms, a crosslinkable group, and an arylamino group of formula (II)

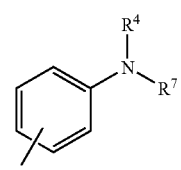

wherein R[4] is selected from aryl, H, R[1], alkyl, and fluoroalkyl. In some embodiments R[4] is aryl. R[7] is selected from aryl, heteroaryl, fluoroaryl, fluoroheteroaryl substituted with 1 or more fluorine atoms, for example, up to 7 fluorine atoms, and a crosslinkable group attached to aryl, heteroaryl, fluoroaryl, and fluoroheteroaryl substituted with 1 or more fluorine atoms, for example up to 7 fluorine atoms. In some embodiments, when $R^1$ or $R^3$ are directly bound to a nitrogen atom, the crosslinkable group is not a vinyl group.

In some embodiments, $R^2$ is H. In some embodiments, $R^2$ is different from $R^3$. In some embodiments, $R^2$ is H and $R^3$ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, fluoroaryloxy, a crosslinkable group, and a crosslinkable group attached to alkyl, aryl, alkoxy, aryloxy, fluoroalkyl, fouoroaryl, fluoroalkoxy, or fluoroaryloxy, and wherein $R^5$ and $R^6$ can, when taken together, form a non-aromatic ring, and E is $(CR^5R^6)_m$, such that when n is greater than 1 and m is 1, at least one of $R^5$ and $R^6$ is not hydrogen or a hydrocarbon.

In some embodiments, at least one aromatic ring in the compound of formula (I) has one or more substituents independently selected from H, F, alkyl, aryl, alkoxy, aryloxy, fluoroalkyl, fluoroaryl, fluoroalkoxy, fluoroaryloxy, and crosslinkable groups. In further embodiments, substituents on two neighboring aromatic rings in the compound of formula (I) can together form an aromatic or non-aromatic ring. Neighboring aromatic rings can be adjacent or vicinal. In further embodiments, adjacent substituents on a single ring can be linked to form a fused aromatic or non-aromatic ring.

In some embodiments, $R^1$ is selected from phenyl, 1-naphthyl, and 2-naphthyl. In some embodiments, $R^1$ is selected from cinnamate and chalcone groups. In some embodiments, n=1, $R^2$ is H, and $R^3$ is selected from phenyl, 1-naphthyl and 2-naphthyl.

In some embodiments, the device is selected from a light-emitting diode, a light-emitting diode display, a laser diode, a photodetector, photoconductive cell, photoresistor, photoswitch, phototransistor, phototube, IR-detector, photovoltaic device, solar cell, light sensor, photoconductor, electrophotographic device, transistor, and a diode.

Another aspect of the present invention is an electronic device having at least one layer comprising a composition comprising a compound of formula

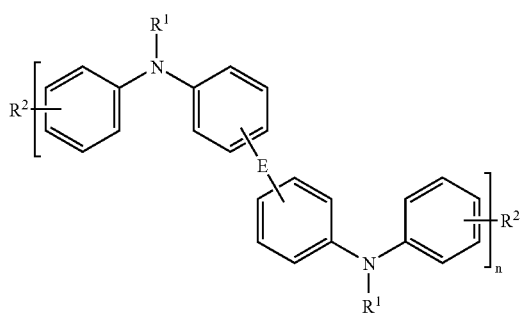

(III)

wherein
n is an integer of at least 1, $R^1$ is selected from aryl, heteroaryl, fluoroaryl, and fluoroheteroaryl substituted with 1 or more fluorine atoms, for example, up to 7 fluorine atoms, and a crosslinkable group attached to aryl, heteroaryl, fluoroaryl, and fluoroheteroaryl substituted with 1 or more fluorine atoms, for example, up to 7 fluorine atoms. $R^1$ may be different at each occurrence (i.e. copolymers). $R^2$ is selected from H, aryl, alkyl, fluoroalkyl, Cl, Br, I, heteroaryl, fluoroaryl, and fluoroheteroaryl substituted with 1 or more fluorine atoms, for example, up to 7 fluorine atoms, a crosslinkable group attached to aryl, heteroaryl, fluoroaryl, fluoroheteroaryl substituted with 1 or more fluorine atoms, for example, up to 7 fluorine atoms, a crosslinkable group, and arylamino of formula (II). In some embodiments, $R^2$ is H or aryl. $R^4$ is selected from aryl, H, $R^1$, alkyl, fluoroalkyl. In some embodiments $R^4$ is aryl or styryl. $R^7$ is selected from aryl, heteroaryl, fluoroaryl, fluoroheteroaryl substituted with 1 or more fluorine atoms, for example up to 7 fluorine atoms and a crosslinkable group attached to aryl, heteroaryl, fluoroaryl, and fluoroheteroaryl substituted with 1 or more fluorine atoms, for example up to 7 fluorine atoms.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, fluoroaryloxy, a crosslinkable group, and a crosslinkable group attached to alkyl, aryl, alkoxy, aryloxy, fluoroalkyl, fouoroaryl, fluoroalkoxy, or fluoroaryloxy, and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments, at least one aromatic ring in the compound of formula (III) has a substituent selected from H, F, alkyl, aryl, alkoxy, aryloxy, fluoroalkyl, fluoroaryl, fluoroalkoxy, fluoroaryloxy, and a crosslinkable group. In further embodiments, substituents on two neighboring aromatic rings in the compound of formula (III) can together form an aromatic or non-aromatic ring. In further embodiments, adjacent substituents on a single ring can be linked to form a fused aromatic or non-aromatic ring.

In some embodiments, $R^1$ is selected from phenyl, 1-naphthyl, and 2-naphthyl. In some embodiments, n=1, and $R^2$ is arylamino of formula (II), wherein $R^4$ is selected from aryl, H, $R^1$, alkyl, and fluoroalkyl. In some embodiments, n=1, $R^1$ is selected from phenyl, 1-naphthyl or 2-naphthyl and $R^2$ is styryl or cinammate. In some embodiments, n=1, $R^1$ is selected from phenyl, 1-naphthyl or 2-naphthyl and $R^2$ is arylamino of formula (II), wherein $R^4$ is selected from aryl, H, styryl or cinamate. In some embodiments, $R^4$ is arylstyryl. In some embodiments, $R^1$ is selected from phenyl, 1-naphthyl or 2-naphthyl and $R^2$ is selected from H or aryl and E is selected from $(CR^5R^6)_m$, wherein $R^5$ is selected from alkyl, aryl, alkoxy and $R^6$ is a crosslinkable group. In some embodiments, when $R^1$ or $R^3$ are directly bound to a nitrogen atom, the crosslinkable group is not a vinyl group.

In some embodiments, the device is selected from a light-emitting diode, a light-emitting diode display, a laser diode, a photodetector, photoconductive cell, photoresistor, photoswitch, phototransistor, phototube, IR-detector, photovoltaic device, solar cell, light sensor, photoconductor, electrophotographic device, transistor, and a diode.

Another aspect of the present invention is an electronic device having at least one layer comprising a composition comprising a compound of formula

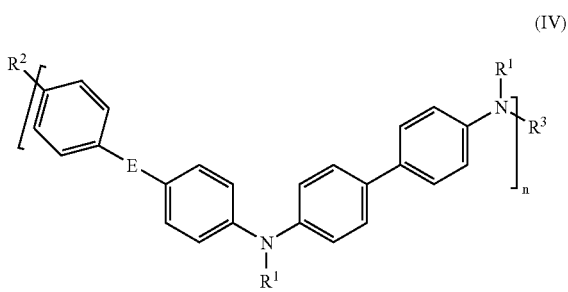

(IV)

wherein:

R¹ is selected from aryl, heteroaryl, fluoroaryl, and fluoroheteroaryl substituted with 1 or more fluorine atoms, for example, up to 7 fluorine atoms, and a crosslinkable group attached to aryl, heteroaryl, fluoroaryl, and fluoroheteroaryl substituted with 1 or more fluorine atoms, for example, up to 7 fluorine atoms, and may be different at each occurrence (i.e. copolymers). In some embodiments, R¹ is aryl. R² is selected from H, aryl, alkyl, fluoroalkyl, Cl, Br, I, heteroaryl, fluoroaryl, and fluoroheteroaryl substituted with 1 or more fluorine atoms, for example, up to 7 fluorine atoms, a crosslinkable group attached to aryl, heteroaryl, fluoroaryl, fluoroheteroaryl substituted with 1 or more fluorine atoms, for example, up to 7 fluorine atoms. In some embodiments, R² is H or a crosslinkable group. R³ is selected from H and R¹. In some embodiments, R³ is aryl. In some embodiments, R² is different from R³. In some embodiments, R² is vinyl and R³ is aryl. R⁴ is selected from aryl, H, R¹, alkyl, fluoroalkyl. In some embodiments R⁴ is aryl. R⁷ is selected from aryl, heteroaryl, fluoroaryl, fluoroheteroaryl substituted with 1 or more fluorine atoms, for example up to 7 fluorine atoms and a crosslinkable group attached to aryl, heteroaryl, fluoroaryl, and fluoroheteroaryl substituted with 1 or more fluorine atoms, for example up to 7 fluorine atoms.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein R⁵ and R⁶ are each independently selected from H, F, alkyl, aryl, alkoxy, aryloxy, fluoroalkyl, fluoroaryl, fluoroalkoxy, fluoroaryloxy, a crosslinkable group, and a crosslinkable group attached to alkyl, aryl, alkoxy, aryloxy, fluoroalkyl, fouoroaryl, fluoroalkoxy, or fluoroaryloxy, and wherein R⁵ and R⁶ can, when taken together, form a non-aromatic ring, provided that when E is $(CR^5R^6)_m$, and n is greater than 1 and m is 1, at least one of R⁵ and R⁶ is not hydrogen or a hydrocarbon.

In some embodiments, at least one aromatic ring in the compound of formula (I) has a substituent selected from H, F, alkyl, aryl, alkoxy, aryloxy, fluoroalkyl, fluoroaryl, fluoroalkoxy, fluoroaryloxy and a crosslinkable group. In some embodiments, R¹ is selected from phenyl, 1-naphthyl, and 2-naphthyl. In some embodiments, n=1, R² is H, and R³ is selected from phenyl, 1-naphthyl and 2-naphthyl, some embodiments, n=1, R¹ is selected from phenyl, 1-naphthyl and 2-naphthyl and R² is a cinammyl group.

In some embodiments, the device is selected from a light-emitting diode, a light-emitting diode display, a laser diode, a photodetector, photoconductive cell, photoresistor, photoswitch, phototransistor, phototube, IR-detector, photovoltaic device, solar cell, light sensor, photoconductor, electrophotographic device, transistor, and a diode.

Another aspect of the present invention is an electronic device having at least one layer comprising composition comprising copolymers prepared by copolymerizing at least one functional monomer having the formula (I) or (III) as defined hereinabove with at least one crosslinkable group as defined above. The polymerization can be performed using thermal or photochemical polymerization methods.

In some embodiments, the composition comprising a compound as disclosed herein is a liquid. The liquid can be in the form of, for example, a solution or dispersion.

A further aspect of the present invention is a process for making an electronic device. The process includes: providing a liquid comprising a compound having the formula (I) as described hereinabove; providing an anode; contacting said liquid comprising said compound with said anode; Removing said liquid from said compound to produce a hole transport film; providing an emitter; disposing said emitter adjacent to said hole transport film; providing an electron transporter and disposing said electron transporter adjacent to said emitter; and providing a cathode adjacent to said electron transporter. The liquid can be, for example, a solution or dispersion.

Unless otherwise defined, all technical and scientific terms used herein have the same meaning as commonly understood by one of ordinary skill in the art to which this invention belongs. Unless otherwise defined, all letter symbols in the figures represent atoms with that atomic abbreviation. Although methods and materials similar or equivalent to those described herein can be used in the practice or testing of the present invention, suitable methods and materials are described below.

All publications, patent applications, patents, and other references mentioned herein are incorporated by reference in their entirety. In case of conflict, the present specification, including definitions, will control. In addition, the materials, methods, and examples are illustrative only and not intended to be limiting.

The foregoing general description and the following detailed description are exemplary and explanatory only and are not restrictive of the invention, as defined in the appended claims.

DESCRIPTION OF THE DRAWINGS

The invention is illustrated by way of example and not limitation in the accompanying figures.

DETAILED DESCRIPTION OF THE PREFERRED EMBODIMENTS

Figure 1:
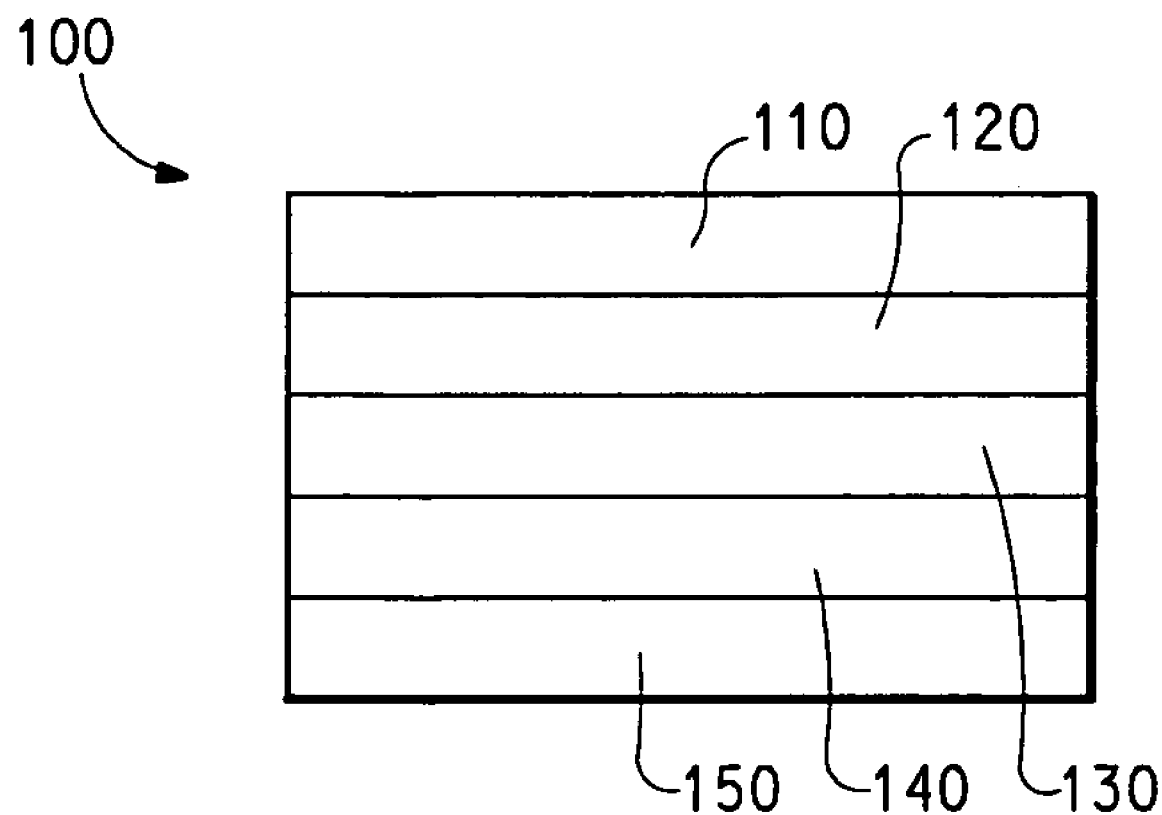
FIG. 1: An illustrative example of one organic electronic device comprising at least one layer comprising a novel compound as disclosed herein.

The compounds disclosed herein are triarylamine derivatives, and can be in the form of dimers, oligomers or polymers, particularly dimers, and contain crosslinkable groups. The compounds can provide the electronic advantages of smaller molecules such as triarylamines, with the solution processability, film forming capabilities, solubility properties, and thermal stability of polymeric compounds. In particular, it has been found that the compounds can be provided in solution and used in solution processes to manufacture electronic devices.

Also provided are compositions containing the compounds, including liquid compositions.

In addition, the compounds can be rendered insoluble subsequent to deposition by thermal or photo-crosslinking reactions. Crosslinked films are generally more robust and resistant to solvents that may be used in later processing steps. Crosslinking groups are well known, and any can be used so long as they do not detrimentally affect the desired properties of the compounds in this invention.

In one embodiment, the electronic devices for which the compounds are useful are OLED devices. In contrast to known compounds such as NPD (N,N'-di(naphthalen-1-yl)-N,N'-diphenyl-benzidine) and TPD (4,4'-bis[N-(3-methylphenyl)-N-phenylamino]biphenyl), which are commonly used as hole transport materials in making electronic devices, generally using vapor deposition processes, the present compounds have improved thermal stability and can be selectively solubilized in common solvents. By selectively solubilized is meant that the compounds can be made to be soluble or substantially soluble in some solvents and insoluble or substantially insoluble in other solvents. For example, in using the compounds to make electronic devices it is often desirable to provide the compound in a solvent in which the compound is soluble or substantially soluble, and deposit thereon another solvent in which the compound is insoluble or substantially insoluble. Solubilization can be provided or enhanced by variation of substituent groups on the compounds.

A suitable solvent for a particular compound or related class of compounds can be readily determined by one skilled in the art. For some applications, it is desirable that the compounds be dissolved in non-aqueous solvents. Such non-aqueous solvents can be relatively polar, such as C1 to C20 alcohols, ethers, and acid esters, or can be relatively non-polar such as C1 to C12 alkanes or aromatics such as toluene, xylenes, trifluorotoluene and the like. Other suitable liquids for use in making a liquid composition, either as a solution or dispersion as described herein, comprising the new compounds, includes, but not limited to, chlorinated hydrocarbons (such as methylene chloride, chloroform, chlorobenzene), aromatic hydrocarbons (such as substituted and non-substituted toluenes and xylenes), including triflurotoluene), polar solvents (such as tetrahydrofuran (THP), N-methyl pyrrolidone) esters (such as ethylacetate) alcohols (isopropanol), keytones (cyclopentatone) and mixtures thereof.

The present invention provides novel compounds, compositions and devices containing the compounds, and methods for making devices containing the compounds. One aspect of the present invention is a composition comprising a compound having the formula:

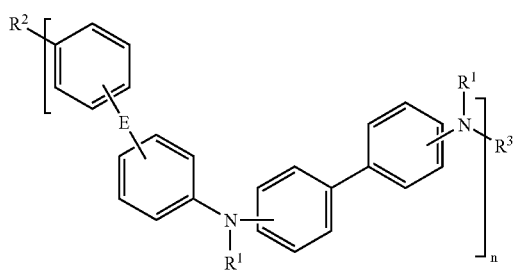

wherein n is an integer of at least 1 and $R^1$ is selected from aryl, heteroaryl, fluoroaryl, and fluoroheteroaryl substituted with 1 or more fluorine atoms, for example, up to 7 fluorine atoms, and a crosslinkable group attached to aryl, heteroaryl, fluoroaryl, and fluoroheteroaryl substituted with 1 or more fluorine atoms, for example, up to 7 fluorine atoms. The compound comprises more than one group $R^1$, and $R^1$ can be different at each occurrence. For example, the compound represented by formula (I) can function as a monomer, and copolymers can be formed from the compound, such copolymers comprising, as polymerized units, a plurality of units having formula (I) in which at least one unit contains $R^1$ different from $R^1$ in other units. In some embodiments, $R^1$ is aryl.

$R^3$ is selected from H and $R^1$. $R^2$ is selected from H, aryl, alkyl, fluoroalkyl, Cl, Br, I, heteroaryl, fluoroaryl, and fluoroheteroaryl substituted with 1 or more fluorine atoms, for example, up to 7 fluorine atoms, a crosslinkable group attached to aryl, heteroaryl, fluoroaryl, fluoroheteroaryl substituted with 1 or more fluorine atoms, for example, up to 7 fluorine atoms a crosslinkable group, and an arylamino group of formula (II),

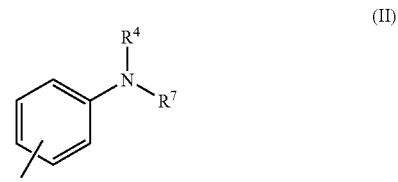

$R^4$ is selected from aryl, H, $R^1$, alkyl, and fluoroalkyl. In some embodiments $R^4$ is aryl. $R^7$ is selected from aryl, heteroaryl, fluoroaryl, and fluoroheteroaryl substituted with 1 or more fluorine atoms, for example, up to 7 fluorine atoms.

In some embodiments, $R^2$ is H. In some embodiments, $R^2$ is different from $R^3$. In some embodiments, $R^2$ is H and $R^3$ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, fluoroaryloxy, a crosslinkable group, and a crosslinkable group attached to alkyl, aryl, alkoxy, aryloxy, fluoroalkyl, fouoroaryl, fluoroalkoxy, or fluoroaryloxy, and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments, at least one aromatic ring in the compound of formula (I) has one or more substituents independently selected from H, F, alkyl, aryl, alkoxy, aryloxy, fluoroalkyl, fluoroaryl, fluoroalkoxy, and fluoroaryloxy. In further embodiments, substituents on two neighboring aromatic rings in the compound of formula (I) can together form an aromatic or non-aromatic ring. In further embodiments, adjacent substituents on a single ring can be linked to form a fused aromatic or non-aromatic ring.

In some embodiments, $R^1$ is selected from phenyl, 1-naphthyl, and 2-naphthyl. In some embodiments, n=1, $R^2$ is H, and $R^3$ is selected from phenyl, 1-naphthyl and 2-naphthyl.

Another aspect of the present invention is a composition comprising a compound of formula

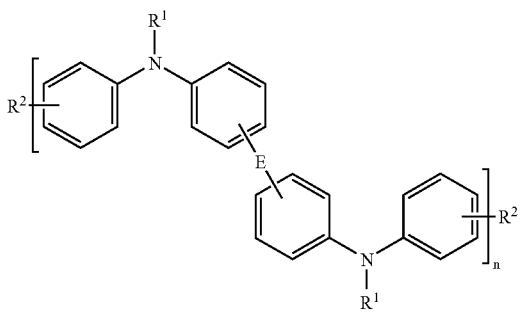

(III)

wherein n is an integer of at least 1, $R^1$ is selected from aryl, heteroaryl, fluoroaryl, and fluoroheteroaryl substituted with 1 or more fluorine atoms, for example, up to 7 fluorine atoms, and a crosslinkable group attached to aryl, heteroaryl, fluoroaryl, and fluoroheteroaryl substituted with 1 or more fluorine atoms, for example, up to 7 fluorine atoms, and may be different at each occurrence (i.e. copolymers). $R^2$ is selected from H, aryl, alkyl, fluoroalkyl, Cl, Br, I, heteroaryl, fluoroaryl, and fluoroheteroaryl substituted with 1 or more fluorine atoms, for example, up to 7 fluorine atoms, a crosslinkable group attached to aryl, heteroaryl, fluoroaryl, fluoroheteroaryl substituted with 1 or more fluorine atoms, for example, up to 7 fluorine atoms a crosslinkable group, arylamino of formula (II).

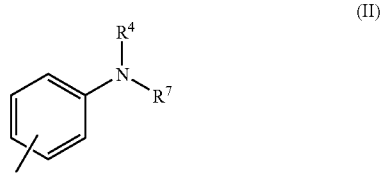

(II)

wherein $R^4$ is selected from aryl, H, $R^1$, alkyl, fluoroalkyl. In some embodiments $R^4$ is aryl. $R^7$ is selected from aryl, heteroaryl, fluoroaryl, fluoroheteroaryl substituted with 1 or more fluorine atoms, for example, up to 7 fluorine atoms, and a crosslinkable group attached to aryl, heteroaryl, fluoroaryl, and fluoroheteroaryl substituted with 1 or more fluorine atoms, for example up to 7 fluorine atoms. In some embodiments, $R^2$ is H or aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, fluoroaryloxy, a crosslinkable group, and a crosslinkable group attached to alkyl, aryl, alkoxy, aryloxy, fluoroalkyl, fouoroaryl, fluoroalkoxy, or fluoroaryloxy, and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments, at least one aromatic ring in the compound of formula (III) has a substituent selected from H, F, alkyl, aryl, alkoxy, aryloxy, fluoroalkyl, fluoroaryl, fluoroalkoxy, and fluoroaryloxy. In further embodiments, substituents on two neighboring aromatic rings in the compound of formula (III) can together form an aromatic or non-aromatic ring. In further embodiments, adjacent substituents on a single ring can be linked to form a fused aromatic or non-aromatic ring.

In some embodiments, $R^1$ is selected from phenyl, 1-naphthyl, 2-naphthyl and styryl. In some embodiments, n=1, x=0, and $R^2$ is arylamino of formula (II), wherein $R^4$ is selected from aryl, H, $R^1$, alkyl, and fluoroalkyl. In some embodiments, $R^4$ is aryl.

Another aspect of the present invention is a composition comprising a compound of formula

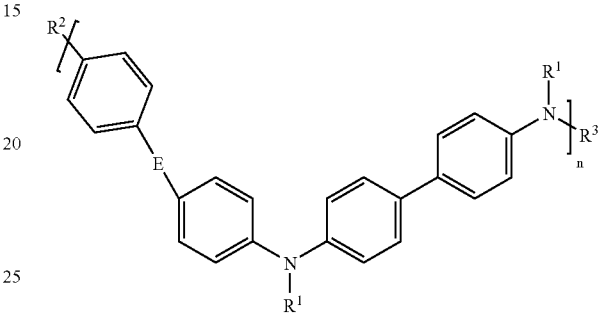

(IV)

wherein $R^1$ is selected from aryl, heteroaryl, fluoroaryl, and fluoroheteroaryl substituted with 1 or more fluorine atoms, for example, up to 7 fluorine atoms, and a crosslinkable group attached to aryl, heteroaryl, fluoroaryl, and fluoroheteroaryl substituted with 1 or more fluorine atoms, for example, up to 7 fluorine atoms, and may be different at each occurrence (i.e. copolymers). In some embodiments, $R^1$ is aryl. $R^2$ is selected from H, aryl, alkyl, fluoroalkyl, Cl, Br, I, heteroaryl, fluoroaryl, and fluoroheteroaryl substituted with 1 or more fluorine atoms, for example, up to 7 fluorine atoms, a crosslinkable group attached to aryl, heteroaryl, fluoroaryl, fluoroheteroaryl substituted with 1 or more fluorine atoms, for example, up to 7 fluorine atoms, a crosslinkable group, Cl, Br, I and an arylamino of formula (II).

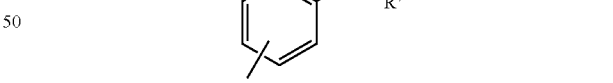

(II)

wherein $R^4$ is selected from aryl, H, $R^1$, alkyl, fluoroalkyl. In some embodiments $R^4$ is aryl. $R^7$ is selected from aryl, heteroaryl, fluoroaryl, fluoroheteroaryl substituted with 1 or more fluorine atoms, for example, up to 7 fluorine atoms, and a crosslinkable group attached to aryl, heteroaryl, fluoroaryl, and fluoroheteroaryl substituted with 1 or more fluorine atoms, for example up to 7 fluorine atoms. In some embodiments, $R^2$ is different from $R^3$. In some embodiments, $R^2$ is H and $R^3$ is aryl. In some embodiments, $R^2$ is H. $R^3$ is selected from H and $R^1$. In some embodiments, $R^3$ is aryl.

E is selected from O, S, $(SiR^5R^6)_m$ wherein m is an integer of 1 to 20, $(CR^5R^6)_m$ wherein m is an integer of 1 to 20, and combinations thereof, and can be different at each occurrence, wherein $R^5$ and $R^6$ are each independently selected from H, F, alkyl, aryl, alkoxy, aryloxy, fluoroalkyl, fluoroaryl, fluoroalkoxy, fluoroaryloxy, a crosslinkable group, and a crosslinkable group attached to alkyl, aryl, alkoxy, aryloxy, fluoroalkyl, fouoroaryl, fluoroalkoxy, or fluoroaryloxy, and wherein $R^5$ and $R^6$ can, when taken together, form a non-aromatic ring, provided that when E is $(CR^5R^6)_m$, and n is greater than 1 and m is 1, at least one of $R^5$ and $R^6$ is not hydrogen or a hydrocarbon.

In some embodiments, at least one aromatic ring in the compound of formula (I) has a substituent selected from H, F, alkyl, aryl, alkoxy, aryloxy, fluoroalkyl, fluoroaryl, fluoroalkoxy, and fluoroaryloxy. In some embodiments, $R^1$ is selected from phenyl, 1-naphthyl, 2-naphthyl and styryl. In some embodiments, n=1, $R^2$ is H, and $R^3$ is selected from phenyl, 1-naphthyl and 2-naphthyl.

The practical upper limit of n in formulas (I), (III) and (IV) is determined in part by the desired solubility of a compound in a particular solvent or class of solvents. As the value of n increases, the molecular weight of the compound increases. The increase in molecular weight is generally expected to result in a reduced solubility of the compound in a particular solvent. Moreover, the value of n at which a compound becomes substantially insoluble in a given solvent is dependent in part upon the structure of the compound. For example, a compound containing multiple phenyl groups may become substantially insoluble in an organic solvent when n is much less than about $10^4$. As another example, a compound containing fewer phenyl groups and/or phenyl groups with particular functional groups may be soluble in a given solvent even though n is about $10^4$ or greater, even $10^5$ or $10^6$. The selection of the value of n and a suitable solvent is within the purview of one skilled in the art.

Also provided are compositions comprising novel copolymers prepared by combining multiple functional monomers. The monomers are units of compounds disclosed herein, which can be polymerized to form the novel copolymers. The monomers can be copolymerized, for example, using a Pd or Ni catalyzed polymerization procedure. Such monomers can be grouped into three classes as follows:

Group 1

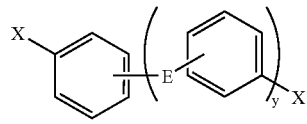

A1

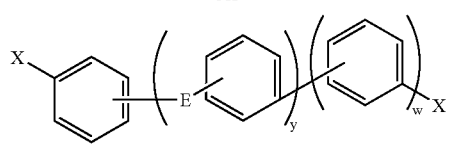

A2

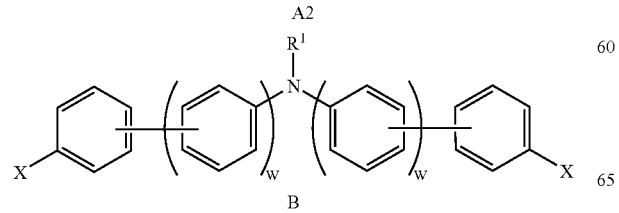

B

-continued

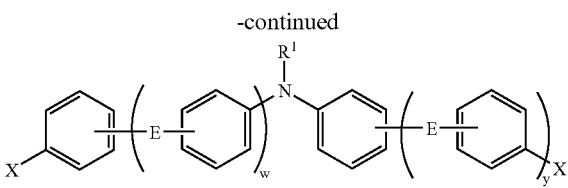

C1

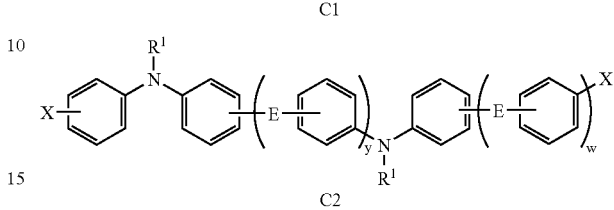

C2

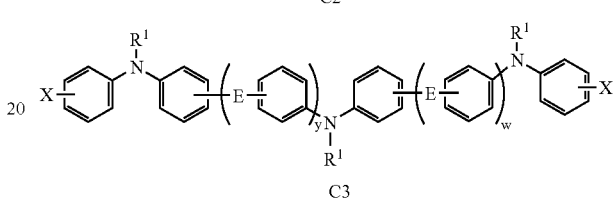

C3 y = 1 or more
w = 0 or more

Group 2

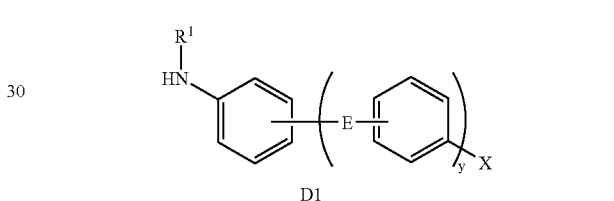

D1

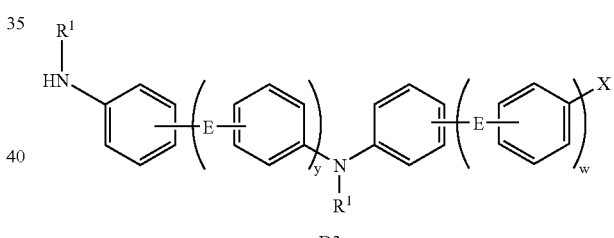

D2

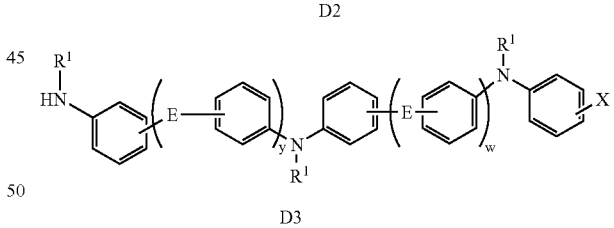

D3

Group 3

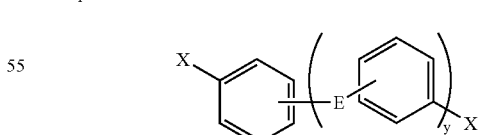

A1

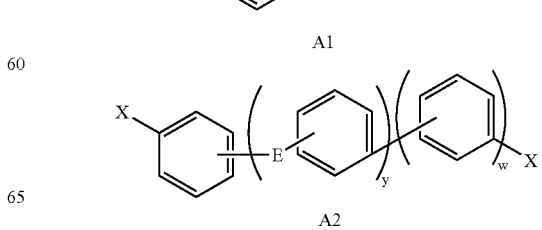

A2

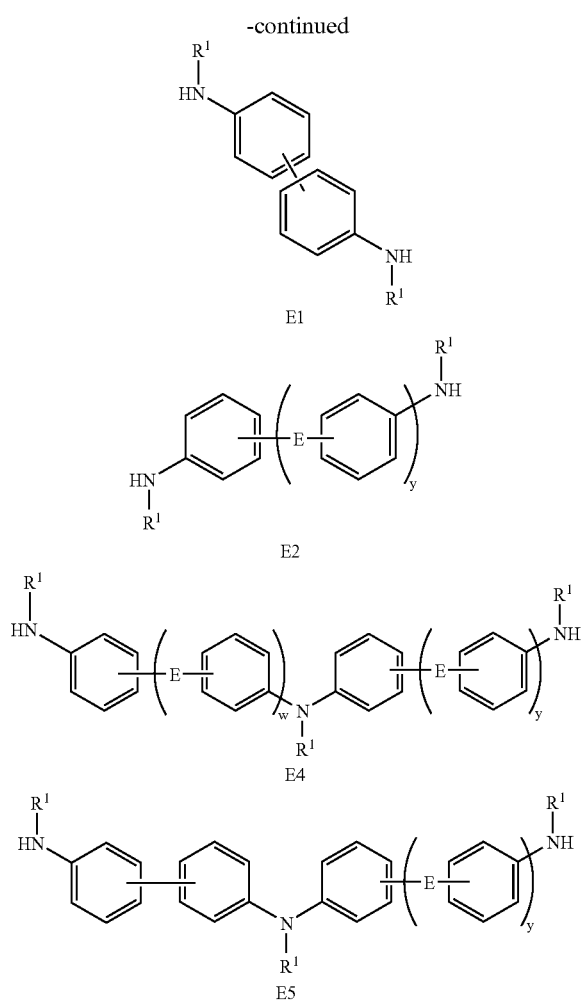

Where y is an integer equal or greater than 1 and w is zero or an integer equal or greater than one, and X is Cl, Br, I, boronic acid, boronic acid ester, boranes or a triflate group; ;and wherein X can be different as each occurrence such that carbon-carbon (for Group 1) and carbon-nitrogen bonds (for Groups 2 and 3) can be formed.

For convenience, exemplary monomers are assigned herein to Group 1, Group 2 or Group 3, and within the Groups, exemplary monomers are assigned to Subgroups such as, for example, within Group 1, subgroups A1, A2, B, C1, C2, and C3.

Copolymers can be made using one or more monomers from each of subgroups within each of Group 1, Group 2, and/or Group 3, provided that no copolymers containing only monomers from subgroups A or copolymers containing only monomers from subgroup B are obtained. Copolymers made from monomers within Group 3 contain at least one comonomer designated A1 or A2, and at least one comonomer from subgroup E1, E2, E3, E4 and E5. Exemplary copolymers include poly(A-co-B); poly(A-co-C); poly(A-co-B-co-C); poly(A-co-C); and copolymers comprising two or more monomers within group C, wherein, for example, "poly (A-co-B)" refers to a copolymer comprising, as polymerized units, monomers in Group A and monomers in Group B. The monomers, e.g., A and B, in such copolymers, can be present in equimolar ratios or in non-equimolar ratios. Copolymers made from monomers in Group 1 are made by formation of carbon-carbon bonds during polymerization. Copolymers made from monomers in Groups 2 and Groups 3 are made by formation of carbon-nitrogen bonds during polymerization.

The copolymers from Group 1 can generally be prepared using known synthetic methods. In one synthetic method, as described in Yamamoto, *Progress in Polymer Science*, Vol. 17, p 1153 (1992), the dihalo derivatives of the monomeric units are reacted with a stoichiometric amount of a zerovalent nickel compound, such as bis(1,5-cyclooctadiene)nickel (0). In another method, as described in Colon et al., *Journal of Polymer Science*, Part A, Polymer chemistry, Edition, Vol. 28, p. 367 (1990), the dihalo derivatives of the monomeric units are reacted with catalytic amounts of Ni(II) compounds in the presence of stoichiometric amounts of a material capable of reducing the divalent nickel ion to zerovalent nickel. Suitable materials include zinc, magnesium, calcium and lithium. In the third synthetic method, as described in U.S. Pat. No. 5,962,631, and published PCT application WO 00/53565, a dihalo derivative of one monomeric unit is reacted with a derivative of another monomeric unit having two reactive groups selected from boronic acid, boronic acid esters, and boranes, in the presence of a zerovalent palladium catalyst, such as tetrakis(triphenylphosphine)Pd.

For example, homopolymers or copolymers containing monomers from Group 2 can be formed by reacting a monomer unit having a reactive primary or secondary amine and a reactive aryl halide in the presence of cupper, nickel or palladium catalysts. Homopolymers or copolymers containing monomers from Group 3 can be produced by the reaction of one or more dihalo monomeric derivative(s) with one or more diamino (primary or secondary) monomeric unit(s) in the presence of cupper, nickel or palladium catalysts. Typical conditions for Pd-catalyzed amination reactions are described in Sadighi, J. P.; Singer, R. A.; Buchwald, S. L. *J. Am. Chem. Soc.* 1998, 120, 4960; Wolfe, J. P.; Tomori, H.; Sadighi, J. P.; Yin, J.; Buchwald, S. L. J., *Org. Chem.* 200, 65, 1158; Hartwig, J. F.; *Modern Arene Chemistry* 2002, 107-168, Astruc, D., Editor, Wiley-VCH Verlag GmbH & Co. KGaA, Weinheim, Germany. Typical conditions for Ni-catalyzed amination reactions are described in Desmarets, C.; Schneider, R.; Fort, Y. *Tetrahedron,* 2001, 57, 6054.; Wolfe, J. P.; Buchwald, S. L., *J. Am. Chem. Soc.* 1997, 119, 4960. Typical conditions for Cu-catalyzed amination reactions are described in Klapars, A.; Antilla, J. C.; Huang, X.; Buchwald, S. L., *J. Am. Chem. Soc.* 2001, 123, 7727.

Oligomers, including dimers, and polymers of the compounds disclosed herein have improved thermal stability in comparison to, e.g., NPD and TPD. For example, a compound of Formula IV wherein $R^1$ is 1-naphthyl and E is $C(CF_3)_2$ generally has a $T_g$ of about 240° C. Typically, the compounds have a $T_g$ of at least about 50° C., generally at least about 100° C.

Compositions of formulas I and IV can be prepared via carbon-nitrogen bond formation methods known to one skilled in the art. For example, homo- or hetero-polymers can be produced by the reaction of one or more dihalo monomeric derivative(s) with equimolar amounts of one or more diamino (primary or secondary) monomeric unit(s) in the presence of copper, nickel or palladium catalysts. Alternatively, one or more monomers containing an amine and a halide as reactive groups can be employed. Typical conditions for Pd-catalyzed amination reactions are described in Sadighi, J. P.; Singer, R. A.; Buchwald, S. L. *J. Am. Chem. Soc.* 1998, 120, 4960.; Wolfe, J. P.; Tomori, H.; Sadighi, J.

P.; Yin, J.; Buchwald, S. L. *J. Org. Chem.* 200, 65, 1158.; Hartwig, J. F. *Modern Arene Chemistry* 2002, 107-168. Editor: Astruc, D., Wiley-VCH Verlag GmbH & Co. KGaA, Weinheim, Germany. Typical conditions for Ni-catalyzed amination reactions are described in Desmarets, C.; Schneider, R.; Fort, Y. *Tetrahedon*, 2001, 57, 6054.; Wolfe, J. P.; Buchwald, S. L. *J. Am. Chem. Soc.* 1997, 119, 4960. Typical conditions for Cu-catalyzed amination reactions are described in Klapars, A.; Antilla, J. C.; Huang, X.; Buchwald, S. L. *J. Am. Chem. Soc.* 2001, 123, 7727.

For example, a diamine monomer E1 from Group 3, such as N,N'-diphenylbenzidine, is reacted with an equimolar amount of a dihalide monomer A1, such as 4,4'-bromophenylisopropylidene, in presence of a suitable base, such as NaO$^t$Bu, catalytic (less than one equivalent) amount of a suitable palladium compound, such as tris(dibenzylideneacetone) dipalladium, and a suitable ligand, such as P($^t$Bu)$_3$. The polymerization is conducted at a temperature between 22° C. to 150° C. for 24 to 92 hours. The resulting polymer is then treated with an endcapping group, such as bromobenzene, and allowed to further react for another 24 to 48 hours to produce a polymer of formula IV, where $R^1$ is phenyl, E is $C(CH_3)_2$ and $R^2=R^3$ is phenyl.

In another example, monomer D1 from Group 2, such as 4-(N-phenylamine)-4'-(bromophenyl)isopropylidene, can be polymerized using conditions described above to give a polymer of formula IV, where $R^1$ is phenyl, E is $C(CH_3)_2$ and $R^2=R^3$ is phenyl.

Compounds of formula III can be prepared via carbon-carbon bond formation methods known to one skilled in the art. In one method, described in Yamamoto, Progress in Polymer Science, Vol. 17, p 1153 (1992), the dihalo derivatives of the monomeric units are reacted with a stoichiometric amount of a zerovalent nickel compound, such as bis(1,5-cyclooctadiene)nickel(0). In the second method, as described in Colon et al., Journal of Polymer Science, Part A, Polymer chemistry Edition, Vol. 28, p. 367 (1990), the dihalo derivatives of the monomeric units are reacted with catalytic amounts of Ni(II) compounds in the presence of stoichiometric amounts of a material capable of reducing the divalent nickel ion to zerovalent nickel. Suitable materials include zinc, magnesium, calcium and lithium. In the third synthetic method, as described in U.S. Pat. No. 5,962,631, and published PCT application WO 00/53565, a dihalo derivative of one monomeric unit is reacted with a derivative of another monomeric unit having two reactive groups selected from boronic acid, boronic acid esters, and boranes, in the presence of a zerovalent palladium catalyst, such as tetrakis(triphenylphosphine)Pd.

For example, a polymeric composition of monomer C2 from Group 1, such as 4,4'-N,N'-[(1-naphthyl)(4-chlorophenyl)]-(hexaflouroisopropylidene) is reacted with a stoichiometric amount of a zerovalent nickel compound, such as bis(1,5-cyclooctadiene)nickel(0), at a temperature between 22° C. to 150° C. for 24 to 92 hours.

For making electronic devices, including OLED devices, in some embodiments the compounds form films when deposited onto a transparent anode such as indium-doped tin oxide (ITO). The quality of the resultant film can be superficially judged by visual/microscopic inspection for smoothness and defect density. In some embodiments that visually observed defects be minimal. Furthermore, film quality can be measured by estimation of film thickness over several separate areas of the film using, for example, an optical ellipsometer or a mechanical profilometer; In some embodiments that the films have substantially uniform thicknesses as measured in the different areas of the film.

The compounds can be used in liquid form, such as a dispersion or solution, in making electronic devices. An exemplary process for making an electronic device includes: providing a liquid comprising a compound having the formula (I) as described hereinabove; providing an anode; contacting said liquid comprising said compound with said anode; Removing said liquid from said compound to produce a hole transport film; providing an emitter; disposing said emitter adjacent to said hole transport film; providing an electron transporter and disposing said electron transporter adjacent to said emitter; and providing a cathode adjacent to said electron transporter.

The liquid is typically a solvent for the compound. For some applications, the compounds can be dissolved in non-aqueous solvents. Such non-aqueous solvents can be relatively polar, such as $C_1$ to $C_{20}$ alcohols, ethers, and acid esters, or can be relatively non-polar such as $C_1$ to $C_{12}$ alkanes. As stated hereinabove, suitable solvents can be readily selected by one skilled in the art.

In one embodiment, the compound is dissolved in a solvent in which the compound is substantially soluble. The solution is then formed into a thin film and dried by any of several known techniques such as spin coating, inkjetting etc. The resultant film formed as the solvent evaporates is then further dried by baking at elevated temperatures above the boiling point of the solvent either in a vacuum of nitrogen atmosphere. The film is then subjected to further processing by depositing a second solution containing emissive layer materials on top of the pre-formed compound film where the emissive materials are dissolved in a solvent in which the compound is substantially insoluble. By "substantially insoluble" is meant that less than about 5 mg of the compound dissolves in 1 ml of the solvent. However, solubilities greater than or less than 5 mg can be used and may be desirable for some applications. For example, a modest solubility up to 10 mg/mL may result in a blurred or graded interface between the HTM polymer of the present invention and the emissive layer materials. Such blurring can have deleterious or beneficial effects depending upon the natures of the materials involved. Such blurring of the interface can result in improved charge transport across the interface and substantially improved device performance or lifetime.

As will be recognized by one skilled in the art, the solubility of a compound is determined in part by substituent groups within the compound. In particular, in the compounds disclosed herein, the nature of the group "E" in the compound can be varied in order to control the solubility of a compound in a particular solvent or class of solvents. Thus, by varying the nature of the group "E", a compound can be modified such that is more or less soluble in water or any given organic non-aqueous solvent.

Also, for making electronic devices, the compounds can have a relatively low solubility, e.g., a solubility less than about 5 mg/mL, even about 2 mg/mL or less, in solvents that can be used to deposit an emissive layer layer film onto an electrode, which is typically a transparent anode such as ITO (indium doped tin oxide).

The present invention also relates to electronic devices comprising at least one layer containing a composition as disclosed herein, as a hole transport layer. The compositions can be in a separate layer, positioned between a photoactive layer and an electrode. Alternatively, a photoactive layer of an organic electronic device can contain the composition. An example of an electronic device that can contain a composition as disclosed herein is shown in FIG. X. The device 100 has an anode layer 110 and a cathode layer 160.

Adjacent to the anode is a layer 120 comprising hole transport material. Adjacent to the cathode is a layer 140 comprising an electron transport and/or anti-quenching material. Between the hole transport layer and the electron transport and/or anti-quenching layer is the photoactive layer 130. In the illustrated embodiment, the device has an optional additional transport layer 150, next to the cathode. Layers 120, 130, 140, and 150 are individually and collectively referred to as the active layers.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary,* 470 and 476 (McGraw-Hill, Inc. 1966).

The compounds disclosed herein are particularly useful in the hole transport layer 120, and as a charge conducting host in the photoactive layer, 130. The other layers in the device can be made of any materials that are known to be useful in such layers. The anode, 110, is an electrode that is particularly efficient for injecting positive charge carriers. It can be made of, for example, materials containing a metal, mixed metal, alloy, metal oxide or mixed-metal oxide, a conducting polymer, or a combination or mixture thereof. Suitable metals include the Group 11 metals, the metals in Groups 4, 5, and 6, and the Group 8-10 transition metals. If the anode is to be light-transmitting, mixed-metal oxides of Group 12, 13 and 14 metals, such as indium-tin-oxide, are generally used. The anode 110 can also comprise an organic material such as polyaniline, as described, for example, in "Flexible light-emitting diodes made from soluble conducting polymer," *Nature* vol. 357, pp 477-479 (11 Jun. 1992). In some embodiments, at least one of the anode and cathode is at least partially transparent to allow the generated light to be observed.

Examples of the photoactive layer 130 include all known electroluminescent materials, including fluorescing and phosphorescing materials (including both organo-metallic complexes and conjugated polymers). Organometallic electroluminescent compounds are used in some embodiments, particularly cyclometalated iridium and platinum electroluminescent compounds and mixtures thereof. Complexes of Iridium with phenylpyridine, phenylquinoline, or phenylpyrimidine ligands are disclosed as electroluminescent compounds in Petrov et al., Published PCT Application WO 02/02714. Other organometallic complexes have been described in, for example, published applications US 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in Synth. Met. (2001), 116 (1-3), 379-383, and Campbell et al., in Phys. Rev. B, Vol. 65 085210. Examples of a few suitable iridium complexes are given in FIG. 6, as Formulae IV(a) through IV(e). Analogous tetradentate platinum complexes can also be used. These electroluminescent complexes can be used alone, or doped into charge-carrying hosts, as noted above. The compounds, in addition to being useful in the hole transport layer 120, electronic transport layer 140/150 can also act as a charge carrying host for an emissive dopant in the photoactive layer 130 or otherwise part of the photoactive layer.

Examples of electron transport materials which can be used in layer 140 and/or layer 150 include metal chelated oxinoid compounds, such as tris(8-hydroxyquinolato)aluminum ($Alq_3$); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and mixtures thereof.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

It is known to have other layers in organic electronic devices. For example, there can be a layer (not shown) between the anode 110 and hole transport layer 120 to facilitate positive charge transport and/or band-gap matching of the layers, or to function as a protective layer. Layers that are known in the art can be used. In addition, any of the above-described layers can be made of two or more layers. Alternatively, some or all of anode layer 110, the hole transport layer 120, the electron transport layers 140 and 150, and cathode layer 160, may be surface treated to increase charge carrier transport efficiency. The choice of materials for each of the component layers can be made by balancing the goals of providing a device with high device efficiency with device operational lifetime.

It is understood that each functional layer may be made up of more than one layer.

The devices can be prepared using a variety of techniques, including sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be applied from solutions or dispersions in suitable solvents, using any conventional coating or printing technique, including but not limited to spin-coating, dip-coating, roll-to-roll techniques, ink-jet printing, screen-printing, gravure printing and the like. Combinations of vapor deposition and solution coating of individual layers can be used. In general, the different layers have the following range of thicknesses: anode 110, 500-5000 Å, frequently 1000-2000 Å; hole transport layer 120, 50-2000 Å, frequently 200-1000 Å; photoactive layer 130, 10-2000 Å, frequently 100-1000 Å; electron transport layer 140 and 150, 50-2000 Å, frequently 100-1000 Å; cathode 160, 200-10000 Å, frequently 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

As used herein, unless expressly otherwise stated, the following terms have the meanings recited below.

The term "charge transport composition" is intended to mean material that can receive a charge from an electrode and facilitate its movement through the thickness of the material with relatively high efficiency and small loss of charge. Hole transport compositions are capable of receiving a positive charge from an anode and transporting it. Electron transport compositions are capable of receiving a negative charge from a cathode and transporting it.

The term "composition", used alone to refer to compositions having particular formulas disclosed and claimed herein, is intended to be construed broadly to include the compounds, monomers, dimers, oligomers and polymers thereof, as well as solutions, dispersions, liquid and solid mixtures and admixtures.

The term "anti-quenching composition" is intended to mean a material which prevents, retards, or diminishes both the transfer of energy and the transfer of an electron to or from the excited state of the photoactive layer to an adjacent layer.

The term "photoactive" refers to any material that exhibits electroluminescence, photoluminescence, and/or photosensitivity.

The term "group" is intended to mean a part of a compound, such as a substituent in an organic compound. The prefix "hetero" indicates that one or more carbon atoms have been replaced with a different atom.

The term "alkyl" is intended to mean a group derived from an aliphatic hydrocarbon having one point of attachment, which group may be unsubstituted or substituted. The term "heteroalkyl" is intended to mean a group derived from an aliphatic hydrocarbon having at least one heteroatom and having one point of attachment, which group may be unsubstituted or substituted.

The term "alkylene" is intended to mean a group derived from an aliphatic hydrocarbon and having two or more points of attachment. The term "heteroalkylene" is intended to mean a group derived from an aliphatic hydrocarbon having at least one heteroatom and having two or more points of attachment.

The term "alkenyl" is intended to mean a group derived from a hydrocarbon having one or more carbon-carbon double bonds and having one point of attachment, which group may be unsubstituted or substituted. The term "alkynyl" is intended to mean a group derived from a hydrocarbon having one or more carbon-carbon triple bonds and having one point of attachment, which group may be unsubstituted or substituted. The term "alkenylene" is intended to mean a group derived from a hydrocarbon having one or more carbon-carbon double bonds and having two or more points of attachment, which group may be unsubstituted or substituted. The term "alkynylene" is intended to mean a group derived from a hydrocarbon having one or more carbon-carbon triple bonds and having two or more points of attachment, which group may be unsubstituted or substituted.

The terms "heteroalkenyl", "heteroalkenylene", "heteroalkynyl" and "heteroalkynylene" are intended to mean analogous groups having one or more heteroatoms.

The term "aryl" is intended to mean a group derived from an aromatic hydrocarbon having one point of attachment, which group may be unsubstituted or substituted. The term "heteroaryl" is intended to mean a group derived from an aromatic group having at least one heteroatom and having one point of attachment, which group may be unsubstituted or substituted.

Unless otherwise indicated, all groups can be unsubstituted or substituted. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "vicinal" means on adjoining atoms in a ring or chain.

The term "compound" is intended to mean an electrically uncharged substance made up of molecules that further consist of atoms, wherein the atoms cannot be separated by physical means.

The term "polymeric" is intended to encompass oligomeric species and include materials having 2 or more monomeric units. In addition, the IUPAC numbering system is used throughout, where the groups from the Periodic Table are numbered from left to right as 1 through 18 (CRC Handbook of Chemistry and Physics, 81$^{st}$ Edition, 2000).

As used herein, "solution processing" means processes that include depositing from a liquid medium. The liquid medium can be in the form of a solution, a dispersion, an emulsion, or other forms.

The term "film" refers to a coating covering a desired area. The area can be as large as an entire display, or as small as a single sub-pixel. Films can be formed by any conventional deposition technique. Typical deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, "the", "a" or "an" are employed to describe elements and components of the invention. This is done merely for convenience and to give a general sense of the invention. This description should be read to include one or at least one and the singular also includes the plural unless it is obvious that it is meant otherwise.

EXAMPLES

The following examples illustrate certain features and advantages of the present invention. They are intended to be illustrative of the invention, but not limiting. All percentages are by weight, unless otherwise indicated.

Example 1

This example illustrates the preparation of one exemplary compound:

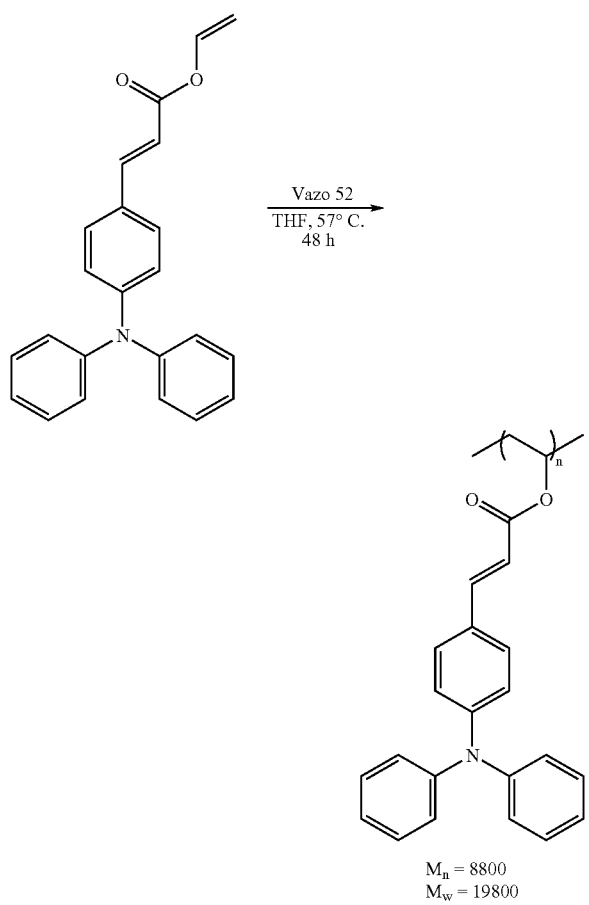

Synthesis of Vinyl Iodoacetate

A 100 mL round bottom flask equipped with a mechanical stirrer and nitrogen inlet-outlet was charged with vinyl chloroacetate (3.83 g, 31.8 mmol) in 50 mLs acetone. Sodium iodide (39.4 mmol) was added resulting in a moderate temperature rise upon initiation of the reaction. The reaction was stirred at room temperature for two days and then concentrated on a rotary evaporator. The residue was dissolved in 100 mL diethyl ether and washed two times with 100 mL water, once with 10 wt % aq. sodium bisulfite (aq.), once with 100 mL water and once with 100 mL saturated aq. NaCl. The organic layer was dried over $MgSO_4$, filtered and concentrated on a rotary evaporator. The residue was further concentrated on a high vacuum line to give 5.6 g product as a light pink oil. The yield was 82%.

Synthesis of Vinyl-4-(N,N-diphenylamino)cinnamate

A 100 mL round bottom flask equipped with a nitrogen inlet-outlet, magnetic stirrer and addition funnel was charged with vinyl iodoacetate (5.6 g, 26 mmol) and triphenylphosphine (6.9 g, 26 mmol) in 50 mL anhydrous tetrahydrofuran. The reaction mixture was blanketed with nitrogen and allowed to stir for 16 h and then cooled to 6° C. on an ice-water bath. Sodium hydride (1.0 g, 25 mmol) was added and the reaction was allowed to warm to room temperature. After stirring at room temperature for 4 h, 4-diphenylaminobenzaldehyde (5.4 g, 20 mmol) dissolved in 40 mL anhydrous THF was added dropwise to the stirring reaction mixture over 30 minutes. After stirring at room temperature for five days, the reaction mixture was diluted with 50 mL diethyl ether and transferred to a separatory funnel. An additional 300 mL diethyl ether was added to the separatory funnel and the combined ether solution was washed three times with 100 mL water and one time with 100 mL saturated NaCl solution. The organic layer was dried over $MgSO_4$, filtered and concentrated on a rotary evaporator. The residue was further dried on a high vacuum line to yield the crude product as a brown oil. After purification by flash column chromatography (silica gel; 3:7 dichloromethane:hexanes) 5.5 g of the pure product was obtained as a light yellow oil. The product yield was 81%.

Synthesis of poly[Vinyl-4-(N,N-diphenylamino)cinnamate]

A clean, dry 25 mL Schlenk tube was equipped with a magnetic stir bar and a septum seal and then charged with vinyl-4-(N,N-diphenylamino)cinnamate (0.86 g, 2.5 mmol), Vazo 52 (5 mg, 0.8 mol %) and tetrahydrofuran (0.86 g). The Schlenk tube was sealed and degassed with three freeze-pump-thaw cycles under nitrogen and then sealed. The contents were heated in a thermostatted oil bath set to 57° C. for 48 h. After this time, the polymerization was allowed to cool and then diluted with 3 mL tetrahydrofuran. The polymer was isolated by precipitation from 80 mL stirring hexanes. The polymer was further purified by flash column chromatography (neutral alumina; 1:1 hexanes:dichloromethane). After removal of solvent, 220 mg of a yellow solid was obtained. The yield was 25.5%. The polymer obtained in this way was free of monomer. The molecular weight of the polymer was determined by gel permeation chromatography. $M_w$=280,900; $M_n$=52,300; $M_w/M_n$=5.37.

Example 2

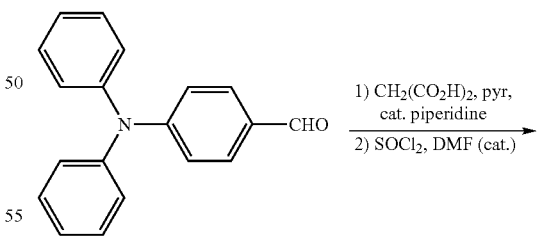

Polymer grafting

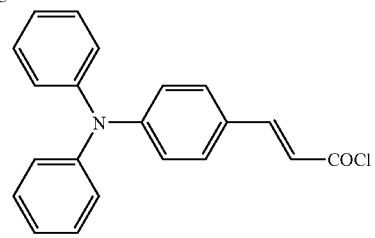

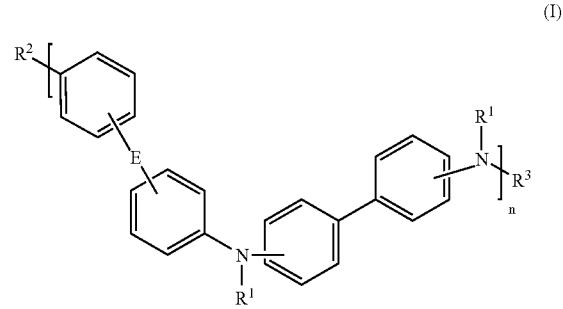

Evanol 71-30
$M_n$ = 46K
$M_w$ = 95k

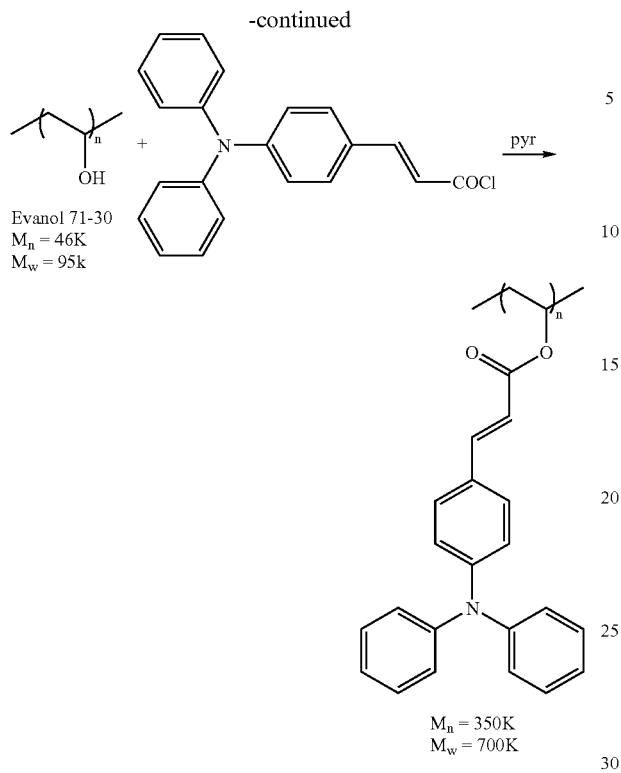

$M_n$ = 350K
$M_w$ = 700K

Synthesis of 4-(N,N-diphenylamino)cinnamic acid

All glassware was dried in a drying oven heated to 140° C. Malonic acid was dried on a high vacuum line over $P_2O_5$ and then stored in a nitrogen purged glovebox. Pyridine (Aldrich, anhydrous, 99.8%) and piperidine were used as received and stored in the glovebox. In a 100 mL round bottom flask equipped with a stir bar, condenser and nitrogen inlet-outlet was dissolved malonic acid (2.3 g, 22.0 mmol) in 20 mL pyridine. 4-(N,N-Diphenylamino)benzaldehyde (5.0 g, 18.3 mmol) was added and addition of 20 mL pyridine was necessary to obtain a solution. Piperidine (0.18 mL, 1.8 mmol) was added and the solution was heated to reflux. After heating for 25 hours, malonic acid (0.60 g, 5.8 mmol) was added and heating was resumed for an additional 2.5 h after which time no further reaction was observed. The reaction mixture was allowed to cool to room temperature and then poured into a stirring mixture of 12 N HCl in ice water (1:5). The mixture was filtered and the solids rinsed three times with 20 mL water. The solids were collected and the crude product was purified by recrystallization from 5:3 hexanes:EtOAc at 4° C. The mother liquor was concentrated and recrystallized in a similar fashion from 7:3 hexanes: ethyl acetate. The combined crops give 3.1 g of a light brown powder. The yield was 55%.

Synthesis of 4-(N,N-diphenylamino)cinnamoyl chloride

A 50 mL round bottom flask equipped with a magnetic stirrer and a nitrogen inlet-outlet was charged with 4-(N,N-diphenylamino)cinnamic acid (1.0 g, 3.2 mmol) in 15 mL dichloromethane. Thionyl chloride (0.35 mL, 4.8 mmol) was added followed by 12.4 □L N,N-dimethylformamide. Hydrogen chloride gas evolution began immediately and then ceased within one hour of stirring. The solution was stirred for 3 h and then concentrated on a rotary evaporator. The product was transferred to a high vacuum line and residual solvent was removed under vacuum. The product was obtained as a brown solid and stored under nitrogen without any further purification.

What is claimed is:

1. A compound having the formula:

(I)

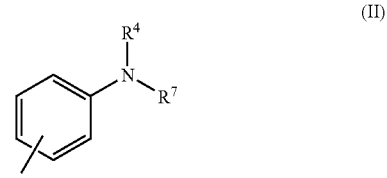

wherein
n is an integer;
$R^1$ is selected from aryl, heteroaryl, fluoroaryl substituted with 1 or more fluorine atoms, fluoroheteroaryl substituted with 1 or more fluorine atoms, and a crosslinkable group attached to aryl, heteroaryl, fluoroaryl, or fluoroheteroaryl substituted with 1 or more fluorine atoms, wherein said crosslinkable group does not include a vinyl group;
$R^2$ is selected from H, aryl, alkyl, fluoroalkyl, Cl, Br, I, heteroaryl, fluoroaryl substituted with 1 or more fluorine atoms, fluoroheteroaryl substituted with 1 or more fluorine atoms; a crosslinkable group attached to aryl, heteroaryl, fluoroaryl substituted with 1 or more fluorine atoms or fluoroheteroaryl substituted with 1 or more fluorine atoms, a crosslinkable group, and an arylamino group of formula (II), (II)

wherein
$R^4$ is selected from aryl, H, $R^1$, alkyl, and fluoroalkyl;
$R^7$ is selected from aryl, heteroaryl, fluoroaryl substituted with 1 or more fluorine atoms, fluoroheteroaryl substituted with 1 or more fluorine atoms, and a crosslinkable group attached to aryl, heteroaryl, fluoroaryl substituted with 1 or more fluorine atoms or fluoroheteroaryl substituted with 1 or more fluorine atoms;
$R^3$ is selected from H and $R^1$;
E is selected from O, S, $(SiR^5R^6)_m$ wherein m is an integer of 1 to 20, $(CR^5R^6)_m$ wherein m is an integer of 1 to 20, and combinations the thereof,
wherein $R^5$ and $R^6$ are each independently selected from H, F, alkyl, aryl, alkoxy, aryloxy, fluoroalkyl, fluoroaryl, fluoroalkoxy, fluoroaryloxy, a crosslinkable group, and a crosslinkable group attached to alkyl, aryl, alkoxy, aryloxy, fluoroalkyl, fluoroaryl, fluoroalkoxy, or fluoroaryloxy, and wherein when E is $(CR^5R^6)_m$, and n is greater than 1 and m is 1, at least one of $R^5$ and $R^6$ is not hydrogen or a hydrocarbon and;

wherein the compound bears at least one crosslinkable group.

2. The compound of claim 1, wherein at least one aromatic ring in the compound of formula (I) has one or more substituents independently selected from F, alkyl, aryl, alkoxy, aryloxy, fluoroalkyl, fluoroaryl, fluoroalkoxy, fluoroaryloxy, and crosslinkable groups.

3. The compound of claim 1, wherein $R^5$ and $R^6$, when taken together, form a non-aromatic ring.

4. The compound of claim 1, wherein two or more substituents on two neighboring aromatic rings in the compound of formula (I) together form an aromatic or non-aromatic ring.

5. The compound of claim 1, wherein adjacent substituents on a single ring are linked to form a fused aromatic or non-aromatic ring.

6. The compound of claim 1, wherein $R^1$ is selected from phenyl, 1-naphthyl, and 2-naphthyl, cinnamate and chalcone groups.

7. The compound of claim 1, wherein n=1, $R^2$ is H, and $R^3$ is selected from phenyl, 1-naphthyl, 2-naphthyl and styryl.

8. A compound of formula (III)

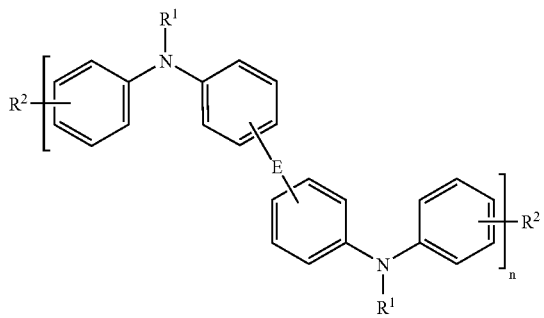

wherein n is an integer, $R^1$ is selected from aryl, heteroaryl, fluoroaryl, and fluoroheteroaryl substituted with 1 or more fluorine atoms, and a crosslinkable group attached to aryl, heteroaryl, fluoroaryl, and fluoroheteroaryl substituted with 1 or more fluorine atoms, $R^2$ is selected from H, aryl, alkyl, fluoroalkyl, Cl, Br, I, heteroaryl, fluoroaryl substituted with 1 or more fluorine atoms, fluoroheteroaryl substituted with 1 or more fluorine atoms, a crosslinkable group attached to aryl, heteroaryl, fluoroaryl substituted with 1 or more fluorine atoms or fluoroheteroaryl substituted with 1 or more fluorine atoms, a crosslinkable group, and arylamino of formula (II)

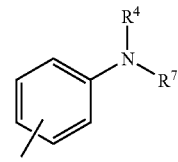

wherein $R^4$ is selected from aryl, H, $R^1$, alkyl, and fluoroalkyl;

$R^7$ is selected from aryl, heteroaryl, fluoroaryl substituted with 1 or more fluorine atoms, fluoroheteroaryl substituted with 1 or more fluorine atoms, and a crosslinkable group attached to aryl, heteroaryl, fluoroaryl, and fluoroheteroaryl substituted with 1 or more fluorine atoms;

E is selected from O, S, $(SiR^5R^6)_m$ wherein m is an integer of 1 to 20, $(CR^5R^6)_m$ wherein m is an integer of 1 to 20, and combinations thereof, wherein $R^5$ and $R^6$ are each independently selected from H, F, alkyl, aryl, alkoxy, aryloxy, fluoroalkyl, fluoroaryl, fluoroalkoxy, fluoroaryloxy, a crosslinkable group, and a crosslinkable group attached to alkyl, aryl, alkoxy, aryloxy, fluoroalkyl, fluoroaryl, fluoroalkoxy, or fluoroaryloxy, provided that when E is $(CR^5R^6)_m$, and n is greater than 1 and m is 1, at least one of $R^5$ and $R^6$ is not hydrogen or a hydrocarbon; and wherein the compound bears at least one crosslinkable group.

9. The compound of claim 8, wherein $R^5$ and $R^6$, when taken together, form a non-aromatic ring.

10. The compound of claim 8, wherein at least one aromatic ring in the compound of formula (III) has a substituent selected from F, alkyl, aryl, alkoxy, aryloxy, fluoroalkyl, fluoroaryl, fluoroalkoxy, fluoroaryloxy, and a crosslinkable group.

11. The compound of claim 8, wherein two or more substituents on two neighboring aromatic rings in the compound of formula (III) together form an aromatic or non-aromatic ring.

12. The compound of claim 8, wherein adjacent substituents on a single ring are linked to form a fused aromatic or non-aromatic ring.

13. The compound of claim 8 wherein $R^1$ is selected from phenyl, 1-naphthyl, and 2-naphthyl.

14. The compound of claim 8, wherein n=1, and $R^2$ is arylamino of formula (II), wherein $R^4$ is selected from aryl, H, $R^1$, alkyl, and fluoroalkyl.

15. The compound of claim 8 wherein n=1, $R^1$ is selected from phenyl, 1-naphthyl or 2-naphthyl and $R^2$ is styryl or cinammate, or arylamino of formula (II), wherein $R^4$ is selected from aryl, H, styryl and cinnamate.

16. The compound of claim 8 wherein $R^1$ is selected from phenyl, 1-naphthyl and 2-naphthyl and $R^2$ is selected from H and aryl and E is selected from $(CR^5R^6)$m, wherein $R^5$ is selected from alkyl, aryl, and alkoxy and $R^6$ is a crosslinkable group.

17. A compound of formula

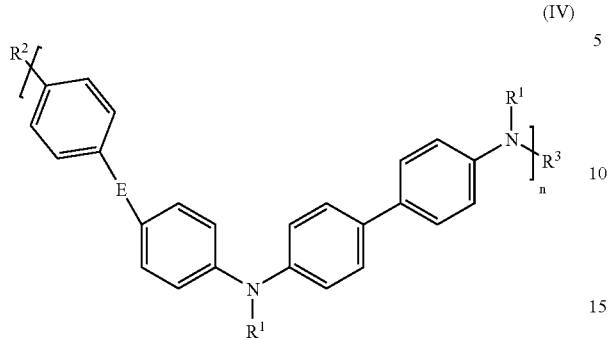

(IV)

wherein:
n is an integer;
R¹ is selected from aryl, heteroaryl, fluoroaryl, and fluoroheteroaryl substituted with 1 or more fluorine atoms, and a crosslinkable group attached to aryl, heteroaryl, fluoroaryl, and fluoroheteroaryl substituted with 1 or more fluorine atoms, wherein said crosslinkable group does not include a vinyl group;
R² is selected from H, aryl, alkyl, fluoroalkyl, Cl, Br, I, heteroaryl, fluoroaryl, and fluoroheteroaryl substituted with 1 or more fluorine atoms, a crosslinkable group attached to aryl, heteroaryl, fluoroaryl substituted with 1 or more fluorine atoms, fluoroheteroaryl substituted with 1 or more fluorine atoms, a crosslinkable group, and an arylamino group of formula (II),

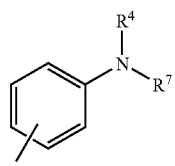

wherein
R⁴ is selected from aryl, H, R¹, alkyl, and fluoroalkyl;
R⁷ is selected from aryl, heteroaryl, fluoroaryl substituted with 1 or more fluorine atoms, fluorohetemaryl substituted with 1 or more fluorine atoms, and a crosslinkable group attached to aryl, heteroaryl, fluoroaryl, and fluoroheteroaryl substituted with 1 or more fluorine atoms;

R³ is selected from H and R¹;

E is selected from O, S, $(SiR^5R^5)_m$ wherein m is an integer of 1 to 20, $(CR^5R^6)_m$ wherein m is an integer of 1 to 20, and combinations thereof,
  wherein $R^5$ and $R^6$ are each independently selected from H, F, alkyl, aryl, alkoxy, aryloxy, fluoroalkyl, fluoroaryl, fluoroalkoxy, fluoroaryloxy, a crosslinkable group, and a crosslinkable group attached to alkyl, aryl, alkoxy, aryloxy, fluoroalkyl, fluoroaryl, fluoroalkoxy, or fluoroaryloxy, provided that when E is $(CR^5R^6)_m$, and n is greater than 1 and m is 1, at least one of $R^5$ and $R^6$ is not hydrogen or a hydrocarbon; and wherein the compound bears at least one crosslinkable group.

18. The compound of claim 17 wherein at least one aromatic ring in the compound of formula (I) has a substituent selected from F, alkyl, aryl, alkoxy, aryloxy, fluoroalkyl, fluoroaryl, fluoroalkoxy, fluoroaryloxy and a crosslinkable group.

19. The compound of claim 17 wherein R¹ is selected from phenyl, 1-naphthyl, and 2-naphthyl.

20. The compound of claim 17 wherein n=1, R² is H, and R3 is selected from phenyl, 1-naphthyl, 2-naphthyl and styryl.

21. The compound of claim 17 wherein $R^5$ and $R^6$, taken together, form a non-aromatic ring.

22. A composition comprising a copolymer prepared by copolymerizing at least one compound of claim 1 and at least one compound of claim 8, said compound of claim 1 or claim 8 comprising at least one crosslinkable group.

23. A composition comprising a compound of claim 1.

24. A composition comprising a compound of claim 8.

25. A composition comprising a compound of claim 17.

26. A copolymer comprising monomers selected from the group consisting of at least one compound of claim 1 and at least one compound of claim 8, said compound of claim 1 or claim 8 comprising at least one crosslinkable group.

* * * * *